US00PP31250P2

(12) United States Plant Patent
Hansen

(10) Patent No.: US PP31,250 P2
(45) Date of Patent: Dec. 17, 2019

(54) **X *MANGAVE* PLANT NAMED 'IRON MAN'**

(50) Latin Name: **x *Mangrave* hybrid, *Manfreda* times *Agave***
Varietal Denomination: Iron Man

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,623

(22) Filed: Dec. 11, 2018

(51) Int. Cl.
*A01H 5/12* (2018.01)
*A01H 6/24* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique x *Mangave* plant named 'Iron Man' characterized by a large mound of broad, fleshy, longitudinally folded, grey-green foliage that is cascading or arches with age. Leaves have large, firm, marginal teeth that leave an imprint on the top and bottom of surrounding leaves in the enrolled apex. Foliage is upright to outwardly toward stem with a tendency to arch in maturity. The new plant is suitable for the garden or as a potted plant in the garden or home.

2 Drawing Sheets

Botanical classification: x *Mangave* hybrid, *Manfreda* times *Agave*.
Variety denomination: 'Iron Man'.

STATEMENT REGARDING PRIOR DISCLOSURES UNDER 37 CFR 1.77(b)(6)

The first public disclosure of the claimed plant, in the form of a sale, was made by Walters Gardens, Inc. on Dec. 15, 2017 to Plant Delights Nursery, Inc. in a private sale. Plants for this sale were obtained from the inventor. No plants of x *Mangave* 'Iron Man' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Iron Man' that was hybridized by the inventor at a wholesale perennial nursery in Zeeland, Mich., USA as a cross between an unreleased, unnamed, proprietary *Manfreda maculosa* x *Agave gypsophila* (not patented) given the breeder code H10-02-02 as the female or seed parent times an unnamed *Agave montana* (not patented) as the male or pollen parent. The cross was performed on Oct. 24, 2012 and seeds were harvested and sown later in January 2013. Through trials at the same nursery the plant was assigned the breeder code 12-85-20. The new plant has been successfully asexually propagated by sterile shoot-tip tissue culture and by basal offsets at the same nursery in Zeeland, Mich. The asexual tissue culture propagation has been found to produce stable and identical plants that maintain all the unique characteristics of the original plant.

BRIEF SUMMARY OF THE INVENTION x *Mangave* 'Iron Man' differs from its parents as well as all other *Manfreda, Agave* and x *Mangave* known to the applicant. The female parent has a shorter habit with foliage that is narrower, thinner in cross section, has smaller marginal teeth, with more significant mahogany spotting and has a more coarsely sinuate margin and extremely wavy leaves. The male parent is more upright in habit, slower growing, with foliage that is shorter, more glaucous, broader, more ovate with larger marginal teeth and larger terminal spines. The nearest comparison plants are 'Catch a Wave' U.S. Plant Pat. No. 29,723, 'Falling Waters' U.S. Plant Pat. No. 30,650, 'Mayan Queen' U.S. Plant patent application Ser. No. 15/932,527, 'Silver Fox' U.S. Plant Pat. No. 29,642, 'Tooth Fairy' U.S. Plant Pat. No. 29,599, 'Whale Tale' U.S. Plant patent application Ser. No. 15/932,526 and the *Agave gypsophila* grandparent (not patented). 'Catch a Wave' has more glaucous blue leaves, with coarse sinuate waving, more concentrated greyed-purple spotting. fewer leaves per stem. 'Falling Waters' has less upright more arching habit with smaller diameter stems, and the foliage is more glaucous and folded. 'Mayan Queen' is shorter in habit and the leaves are more glaucous, shorter and bluish colored with more intense purple spotting. 'Silver Fox' has shorter habit, the foliage is more glaucous blue with intense purple spotting and the marginal and terminal spines are more flexible. 'Tooth Fairy' has shorter habit and foliage with leaves more ovate and larger teeth and terminal spines. The *Agave gypsophila* grandparent has coarse sinuate leaf margins, bluer foliage, fewer leaves, and slower growing.

The new plant, 'Iron Man', is unique from all of the above cultivars and all *Agave*, x *Mangave* and *Manfreda* known to the inventor by the following combined traits:

1. Large mound of glaucous, initially dark, glossy, green in youth becoming pulverulent bluish-green in maturity, lanceolate, broad, sarcous leaves;
2. Leaf margins have large, firm, marginal teeth;
3. The teeth leave an imprint on the top and bottom of surrounding leaves from the position in the tightly enrolled apex;

4. Moderate to slow growth rate;
5. Foliage is upright to outwardly toward stem and arches with age.

BRIEF DESCRIPTION OF THE DRAWING

The photograph of x *Mangave* 'Iron Man' demonstrates the overall appearance of the new plant including the unique traits as a five-year-old plant grown in a trial research bed in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
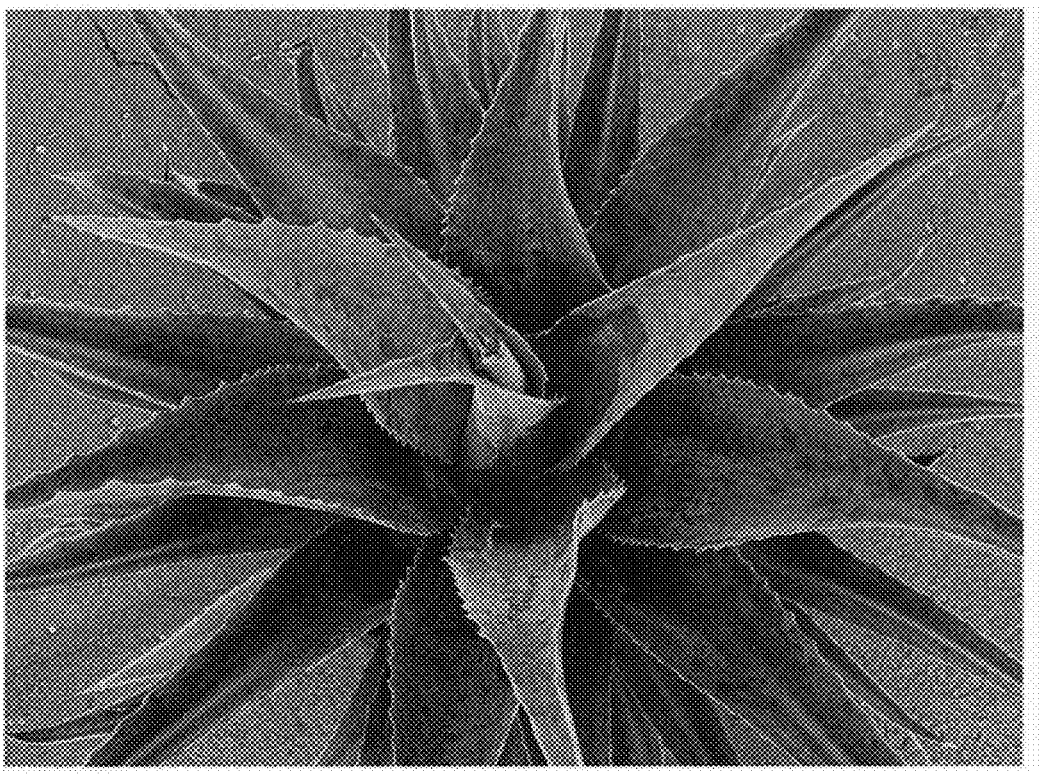
FIG. 1 shows a top view of a five-year-old containerized plant that was grown in a full-sun trial garden.
Figure 2:
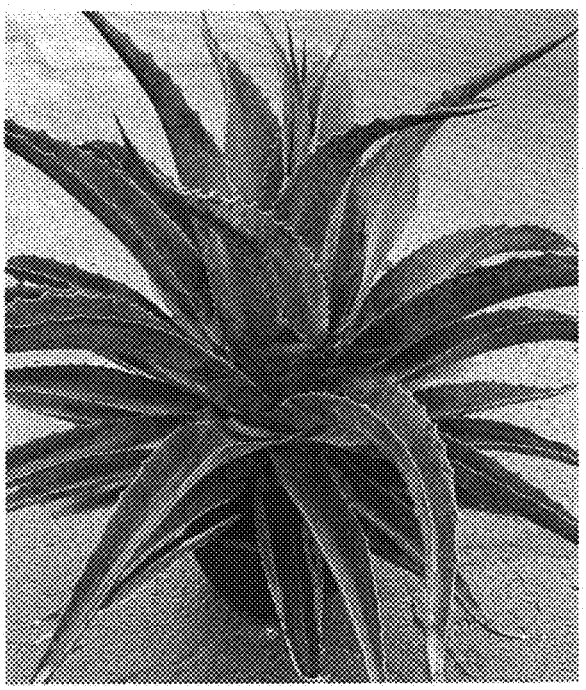
FIG. 2 shows a side view of a five-year-old containerized plant that was grown in a full-sun trial garden.
Figure 3:
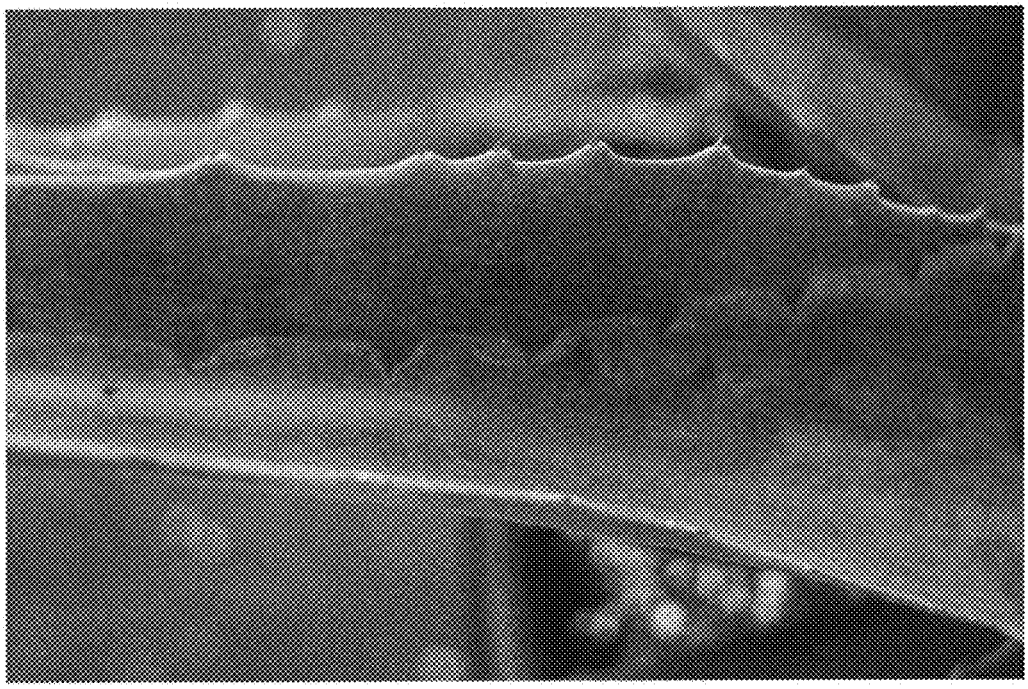
FIG. 3 shows a close-up of the foliage of a five-year-old plant with flat margins, and heavily folded leaves with small teeth barbs and teeth imprints on top of young leaf.

The following descriptions and color references are based on the 2015 edition of The Royal Horticultural Society Colour Chart except where common dictionary terms are used. The new plant, x *Mangave* 'Iron Man', has not been observed under all possible environments. The phenotype may vary slightly with different environmental conditions, such as temperature, light, fertility, moisture and maturity levels, but without any change in the genotype. The following observations and size descriptions are of a five-year-old plant in a commercial wholesale greenhouse in Zeeland, Mich. with supplemental water and fertilizer as needed.

Parentage: H10-02-02, an unnamed select form of *Manfreda maculosa* times *Agave gypsophila* as female or seed patent and an unnamed selection of *Agave montana* as the male or pollen parent;

Propagation: By sterile shoot-tip tissue culture;

Time to initiate roots from tissue culture: About 21 days;

Growth rate: Moderate to slow;

Crop time: About 16 to 20 weeks to finish in a 3.8 liter container from a 35 mm tissue culture growing at about 21° C.;

Rooting habit: Fleshy, lightly branching, with roots up to 30 cm long;

Root color: Nearest RHS 158C;

Plant shape and habit: Succulent herbaceous perennial with basal rosettes of about 56 leaves radially emerging outwardly from central stem, producing a radially-symmetrical, rounded mound;

Plant size: Foliage height about 71.0 cm tall from soil line to the top of the leaves and about 117.0 cm wide at the widest point about middle of the plant;

Foliage description: Lanceolate; simple; sessile; bi-laterally symmetrical; sarcous with low fibrous content inside of leaf; apex narrowly acute with terminal spine; firm terminal spine to about 20.0 mm long and 4.0 mm wide at base; base truncate; slightly conduplicate; margins mostly flat; margins coarsely dentate with large firm teeth; glabrous abaxial and adaxial; glaucous abaxial and adaxial proximally toward stem becoming lustrous in distal two-thirds of leaves both abaxial and adaxial; slightly conduplicate in proximal one-half becoming highly conduplicate to almost parallel leaf sides in distal one-third;

Marginal teeth: Firm; about 5.0 mm long and 7.0 mm wide at base of total tooth projection and barb ends about 1.0 mm long and 1.0 mm wide, about 17.0 mm apart in center on mature leaves;

Leaf size: To about 50.0 cm long, about 14.0 cm wide toward middle; center base about 14.0 mm thick at basal midrib; average about 44.0 cm long, 12.0 cm wide and 4.0 mm thick in longitudinal center;

Foliage fragrance: None observed;

Leaf number: About 56 per plant;

Leaf blade color:

*Adaxial* (*mature*).—With glaucous bloom removed nearest RHS 139A, with glaucous bloom nearest RHS 188B with undertone of nearest RHS 139A.

*Abaxial* (*mature*).—With glaucous bloom removed nearest a blend of RHS 137 B and RHS 146B, with glaucous bloom nearest RHS 188B with undertone of nearest RHS 137B.

*Adaxial* (*young*).—With glaucous bloom nearest a blend between RHS 122B and RHS 188B.

*Abaxial* (*young*).—With glaucous bloom nearest a blend between RHS 122B and RHS 188B.

*Teeth*.—Nearest RHS N172B at base and tips nearest RHS 175A.

*Terminal spine*.—Nearest RHS 178B.

Petiole: Leaves sessile;

Veins: Parallel; not distinct abaxial or adaxial;

Flower description: Not yet observed;

Fruit and seed not observed;

Disease resistance: x *Mangave* 'Iron Man' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Iron Man' as herein described and illustrated.

* * * * *